US007402731B2

(12) United States Patent
Penner et al.

(10) Patent No.: US 7,402,731 B2
(45) Date of Patent: Jul. 22, 2008

(54) IDENTIFICATION OF SEEDS OR PLANTS USING PHENOTYPIC MARKERS

(75) Inventors: Greg A. Penner, Manitoba (CA); Stefan A. Bledig, Chesterfield, MO (US); Timothy W. Conner, Chesterfield, MO (US); Vergel C. Concibido, Maryland Heights, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1036 days.

(21) Appl. No.: 10/071,272

(22) Filed: Feb. 8, 2002

(65) Prior Publication Data

US 2003/0056243 A1    Mar. 20, 2003

Related U.S. Application Data

(60) Provisional application No. 60/327,801, filed on Oct. 9, 2001, provisional application No. 60/267,551, filed on Feb. 9, 2001.

(51) Int. Cl.
    *A01H 1/00*    (2006.01)
(52) U.S. Cl. .................................................. 800/266
(58) Field of Classification Search ................ 800/312; 47/58.1
    See application file for complete search history.

(56) References Cited

U.S. PATENT DOCUMENTS

| 4,627,192 | A |   | 12/1986 | Fick |  |
|---|---|---|---|---|---|
| 5,491,081 | A | * | 2/1996 | Webb | 800/267 |
| 5,764,819 | A | * | 6/1998 | Orr et al. | 382/110 |
| 5,852,226 | A | * | 12/1998 | Fuller et al. | 800/260 |
| 5,859,349 | A | * | 1/1999 | Raque | 800/300 |
| 5,991,025 | A | * | 11/1999 | Wright et al. | 356/328 |
| 5,994,621 | A | * | 11/1999 | Raque | 800/300 |
| 6,008,437 | A |   | 12/1999 | Krebbers et al. |  |
| 6,046,385 | A |   | 4/2000 | Davis |  |
| 6,096,944 | A |   | 8/2000 | Vierling et al. |  |
| 6,100,030 | A |   | 8/2000 | McCasky Feazel et al. |  |
| 6,212,824 | B1 | * | 4/2001 | Orr et al. | 47/58.1 R |
| 6,403,865 | B1 | * | 6/2002 | Koziel et al. | 800/302 |
| 6,865,556 | B2 | * | 3/2005 | Penner et al. | 705/59 |
| 2001/0011437 | A1 | * | 8/2001 | Shortridge et al. | 47/58.1 |
| 2002/0157143 | A1 | * | 10/2002 | Concibido et al. | 800/312 |
| 2003/0041513 | A1 | * | 3/2003 | Okada et al. | 47/58.1 R |
| 2003/0126635 | A1 | * | 7/2003 | Penner et al. | 800/278 |
| 2004/0040055 | A1 | * | 2/2004 | Clair et al. | 800/278 |
| 2004/0040060 | A1 | * | 2/2004 | Clair | 800/281 |
| 2004/0088330 | A1 | * | 5/2004 | Pickett et al. | 707/104.1 |
| 2005/0032033 | A1 | * | 2/2005 | Winterboer et al. | 435/4 |

FOREIGN PATENT DOCUMENTS

| WO | WO 92/01366 | 2/1992 |
| WO | WO 97/14807 | 4/1997 |
| WO | WO 99/60129 | 11/1999 |
| WO | WO 00/71993 A1 * | 11/2000 |

OTHER PUBLICATIONS

Takahashi, R. et al. "Genetic and linkage analysis or low temperature-induced browning in soybean seed coats." The Journa of Heredity V. 85 Nov./Dec. 1994 p. 447-50 (abstract).*
Campbell, Neil A. Biology. The Benjamin/Cummings Publishing Company. Redwood City, CA 1993, pp. 670-671.*
Williams, L.F. "The inheritance of certain black and brown pigments in the Soybean." Genetics 37:208-215 (1952).*
Steyer, Robert "Biotech Battle Opens Way for Test-Makers" St. Louis Post-Dispatch NEWS A8 Sep. 19, 1999.*
Knox, Andrea "Modified Plants or the Real McCoy? A Newark, Del. Company has Developed an Inexpensive Test That is Fast and Easy Enough to use at a Grain Elevator" Philadelphia Inquirer Sep. 19, 1999 Edition D Business C-01.*
Stroud, Jerri. "Farmers Heed Customers' Doubts About Genetically Altered Crops Many Overseas Buyers Demand, and Will Pay More, for the Real Stuff Farmers Say Altered is Better" St. Louis Post-Dispatch Feb. 13, 2000 Business p. E1.*
Lewers et al 1996 Crop Science 36:1560-1567.*
Garcia, et al.; Pollen Control During Transgenic Hybrid Maize Development in Mexico, *Crop Science* 38(6): 1597-1602 (Nov. 1998).
Selinger et al.; A Mutation in the Pale Aleurone Color1 Gene Identifies a Novel Regulator of the Maize Anthocyanin Pathway, *The Plant Cell* 11(1): 5-14 (Jan. 1999).
Selinger et al.; The Maize Regulatory Gene *B-Peru* Contains a DNA Rearrangement That Specifies Tissue-Specific Expression Through Both Positive and Negative Promoter Elements, *Genetics* 149(2): 1125-1138 (Jun. 1998).
Olson, Joan, "Accessing Seed Technologies Will Your Local Seed Supplier Have the Seeds You Want?", Farm Industry News, Dec. 1998.

* cited by examiner

*Primary Examiner*—David H. Kruse
(74) *Attorney, Agent, or Firm*—Howrey LLP

(57) ABSTRACT

Utilizing phenotypic markers in seeds or plants to allow qualitative detection of a proprietary trait in the harvest, to allow a quantitative calculation of the amount of the trait, and to facilitate the calculation and collection of fees for the trait. The phenotypic markers of the seeds can be the seed coat color, and said seeds can be homozygous or heterozygous for the phenotypic difference of seed coat color. Commercial cultivars of seeds with the phenotypic difference of seed color may be grown to include several different seed colors. Trait fees may be assessed on all grain with the proprietary trait, whether the grain was produced from purchased seed or from seed saved from a previous harvest.

11 Claims, No Drawings

IDENTIFICATION OF SEEDS OR PLANTS USING PHENOTYPIC MARKERS

This application claims the benefit of U.S. Provisional Application No. 60/267,551, filed Feb. 9, 2001, and U.S. Provisional Application No. 60/327,801, filed Oct. 9, 2001.

BACKGROUND OF THE INVENTION

1. Field of the Invention

The present invention is generally directed to a method of using phenotypic markers in commercial seed or plant cultivars containing proprietary traits, without actually physically linking the marker to the presence or absence of the proprietary trait, to facilitate the identification of the harvested grain, and further allowing a collection of fees for the proprietary traits based on the presence of the marker in the harvested grain.

2. Background

The introduction of genes into plants, either through genetic transformation or through marker assisted breeding, results in the development of cultivars with improved characteristics. These improvements include such characteristics as enhanced agronomic performance or value-added end-use properties.

It is well known in the art that a phenotypic difference such as leaf color or seed coat color may distinguish a plant or seed line from other similar lines. An alternate seed coat color has been incorporated into the genes of sunflower seeds in U.S. Pat. No. 4,627,192 (Fick). However, many plants that have been improved through technological manipulation may not be visually distinguishable from unimproved plants. The lack of easily distinguishable characteristics makes it difficult to collect a fee for the proprietary trait or traits, or to otherwise track harvested grain containing the trait.

The current methods of generating seed cultivars with a phenotypic leaf color or seed coat color are labor intensive and impractical. The flowering habits of the plants constrain the process. Hand pollination is expensive and time consuming. The use of genetic male sterility systems requires complex methods of female seed increase, thus placing significant constraints on plant breeding and necessarily results in hybrids that segregate for male fertility.

Thus, there exists a need and desire for a simple method of detecting the presence of proprietary traits in plants, seeds, or harvested grain to facilitate collection of fees for the proprietary traits. A method of efficiently generating large quantities of seed cultivars with a phenotypic leaf color or seed coat color is also desired.

SUMMARY OF THE INVENTION

Commercial seed of cultivars containing proprietary traits are produced in a normal manner. Seeds useful in the present invention may contain one or more proprietary traits. Prior to the sale of such proprietary seed to growers, generic or proprietary seed containing a phenotypic marker, such as the black seed coat color in soybeans, are mixed with the seed containing the proprietary trait at a certain low percentage between about 0.1% and 10% by weight and preferably about 0.5% to 4% by weight of the total seed mixture. Upon the purchase of the seed mixture with phenotypic markers, a grower would agree to pay a fee for the proprietary trait in the grain, as indicated by the presence and/or quantity of the phenotypic marker within the grain.

An example of a plant seed mix according to the instant invention comprises about 90% to about 99.9% by weight of primary seeds for a plant variety with a genetically modified trait. These primary seeds would have the seed coat color that is dominant for the plant variety. The plant seed mix also comprises about 0.1% to about 10% by weight of secondary seeds of the same or different plant variety. Such secondary seeds would have a seed coat color with at least one phenotypical difference from the primary seed coat color.

The generation of large amounts of hybrid (F1) seeds by the present invention relies on the use of a combination of herbicide resistance and seed coat color. One example of a herbicide resistant soybean developed by Monsanto Company that is useful in carrying out this invention is sold under the trademark Roundup Ready®, however any herbicide resistant soybean can be used. An example of a seed coat color gene useful in the present invention is the black seed coat color gene encoded by the i allele at the I locus. This gene is expressed in a recessive manner in the seed coat and is therefore expressed in a maternal manner in seeds.

The method of mixing generic seed with seed containing a phenotypic marker improves the enforcement of contracts between the trait proprietor and licensee and also improves the detection of patent and or contract infringement. The present invention also facilitates an end-point value capture system that could result in the trait proprietor being more willing to allow newer technology to be used by the licensee. The present invention enables end-point value capture even if growers mix grain containing a proprietary trait with grain not containing a proprietary trait. The present invention also improves the trait proprietor's ability to collect licensing fees from grower saved seed. Additionally, the present invention allows the detection of the proprietary trait by enabling the reappearance of the phenotypic marker in the subsequent generation after attempts have been made to remove it from a seed lot by physical sorting.

A plant seed mixture useful in the present invention may contain primary colored seeds and secondary colored seeds from the plant species of soybean, canola, or wheat. If soybeans are used, the secondary seed coat colors may be black, brown, heterozygous yellow, or determined by measuring the total light reflectance with a spectrophotometer for wavelengths from 550 to 650 nanometers.

The secondary colored seeds may be generated by planting homozygote black seed coat soybean plants in separate, alternate rows and increasing the seed over several generations, or by separating the black seed coat seeds after the first generation and only propagating them. An additional method of generating secondary colored seeds involves mixing herbicide resistant seeds with non-herbicide resistant seeds; planting and growing the seeds; and spraying the plants with a herbicide such that only a mix of herbicidally culled seeds are left. The primary colored seeds are then separated and retained from the mix.

A seed mixture containing primary and secondary colored seed coat may be used in a method of identifying seed with a proprietary trait by planting and growing the seed mixture; harvesting the grain from the plants; and taking a sample of the grain to determine the amount of phenotypical marker present. Licensing fees may be calculated based on the amount of phenotypical marker present in the grain. A grower may receive a voucher or rebate based on the amount of marker present in the grain.

One skilled in the art may appreciate that this approach facilitates or enables trait identification and fee collection from grain produced from grain produced from proprietary seed, whether the planted seed was purchased or saved from a prior harvest.

DETAILED DESCRIPTION OF PREFERRED EMBODIMENTS

The following terms and phrases are used herein and are intended to have the following meaning:

"end-point value capture" is the assessment and collection of trait fees at the point of grain delivery following harvest, generally a primary elevator;

"proprietary trait" is a trait for which a patent position is held, and/or is managed as a trade secret by the proprietor;

"saved seed" refers to seed that is saved by a grower for replanting in subsequent years;

"licensing fees" are equivalent to royalties paid by the user for the right to use the proprietary trait;

"licensee" is the purchaser of a proprietary trait who has signed a contract with the owners of the proprietary trait which governs terms and conditions for the use of the trait, and the form of renumeration for the right to use the trait;

"trait proprietor" is the owner and/or seller of the proprietary trait;

"brown bag seed" is seed that has been harvested by one grower and sold to another grower for the purpose of planting and harvesting a crop;

"elevator" is the primary commercial delivery point for harvested grain;

"seed coat" is the remnants of the outer integuments of a plant flower, and as such is genetically identical to the plant on which the seed is borne;

"outcrossing" is the fertilization of one plant by another plant possessing a different genetic makeup for the desired phenotypic marker;

"outcrossed seed" is seed produced by a plant which as been fertilized by another plant possessing a different genetic makeup for the desired phenotypic marker;

"selfed seed" is seed produced by a plant which has been fertilized by another plant possessing the same genetic makeup for the desired phenotypic marker;

"grain" is harvested seed sold for commercial purposes;

"grower" is the person responsible for planting, maintaining and harvesting a crop;

"visibly detectable trait" is a trait that can be seen to be different without a need for secondary analysis involving crushing of tissue, or the extraction of any compound;

"sorted seed" is the act of physically differentiating seed based on observation of a visibly detectable trait;

"variety" is a grouping of plants that are homogeneous and stable, and clearly distinguishable by at least one phenotypic characteristic from all other groupings of plants;

"herbicidally culled seed" is seed which is selected as a result of herbicide application;

"F1 seed" is the first generation of seeds produced;

"F2 seed" is the second generation of seeds produced by replanting all or part of the F1 seed either with or without incorporating other seed cultivars.

The present invention is directed to a method of using phenotypic markers in proprietary seed or plant cultivars to facilitate (1) detection of harvested grain containing the proprietary trait and (2) determination of licensing fees.

In one embodiment, the method includes the use of phenotypic markers in soybeans.

Soybean seed coat genetics have been taught by Nagai, Woodworth, and Williams in several publications over the years, the contents of which are incorporated by reference. In soybeans, the gene "R" encodes black seed coat color. "R" is completely dominant to "r" which is the gene for brown seed coat color. A second locus initially designated "C-c" but subsequently designated "T-t", alters black to "imperfect black" and brown to "buff". Woodworth demonstrated that this gene had a pleiotropic effect. Tawny pubescent varieties "T" have black or brown seed coats. Gray pubescent varieties "tt" have imperfect black or buff seed coats.

RT—Black seed coat
rT—Brown seed coat
Rt—Imperfect black seed coat
rt—buff seed coat In addition, Williams found that there is a flower color gene, "W1-w1" that can affect this as well.

RtW1—imperfect black
Rtw1—buff

The following genes are also know to affect soybean seed coat color:

$r^m$—allelic to R (R>$r^m$>r)
$r^m$T—black and brown stripes in concentric rings around the hilum
$r^m$t—hard to distinguish, but exhibits faint rings of black and brown stripes in concentric rings around the hilum.

and

O-o—a separate locus wherein the genotype
orT—produces a dark reddish brown seed coat Additionally, there is the "i" locus which has at least four known alleles.

i—results in the seed coat colors described above
$i^k$—results in a saddle shape pattern of colors localized around the hilum
$i^i$—dark hilum—other colors restricted to the hilum
I—light hilum—color is restricted to the hilum and intensity reduced Another locus k, now designated as k2, was found in the variety Kurakake, ii k—saddle pattern
($i^i$, ik, I)—self black One skilled in the art will appreciate that this locus appears to be some sort of suppressor of more active forms of "i".

Seed color may be measured using a Technicon near-infrared reflectance (NIR) spectrophotometer calibrated to determine total light reflectance (optical density) from 550 to 650 nanometers. This wavelength setting allows separation of yellow from brown from black seeds. Alternatively, optical scanning technology can be used to distinguish seeds on the basis of color. Both NIR and optical scanning can be set up for high-throughput analysis.

Most commercial soybean cultivars exhibit a yellow seed coat color. Soybean seeds with a black coat color occur in approximately one in ten thousand seeds in nature. The black seed coat phenotype is encoded by the presence of homozygous "ii". "R" and "T" are present in commercial germplasm and "i" works by allowing the expression of R across the entire seed coat. In commercial varieties, "I" suppresses all color expression which results in a light colored hilum and prevents color expression outside of the hilum region. In one embodiment of the present invention, the black seed coat soybean cultivars of the present invention are believed to have the genotype, RRiiTT.

The seed coat is maternal tissue in that it is derived from somatic tissue from the plant in which the seed is set. One of skill in the art can recognize that the seed coat color reflects the genotype of the mother plant, not the genotype of the seed itself. Thus, it is possible to generate a seed with a completely yellow seed coat which is homozygous for the black seed coat gene "ii" and which will give rise to black seed coat seeds only as a result of self-pollination or pollination by another homozygous ii plant.

In another descriptive embodiment of the present invention, the plant species is canola. Commercial canola grain generally have black seed coats. Yellow seed coat types are known, and have been related to increased oil and protein contents in *Brassica napus*. Van Deynze and Pauls teach the genetics of canola seed coat colors, the contents of which are incorporated by reference. The inheritance of the yellow seed coat trait in canola appears to be influenced by three recessive nuclear genes (a, b and c).

The presence of the dominant allele at the A locus is sufficient for black seed coat color. The presence of the dominant allele at either the B or C locus is sufficient for brown seed coat color.

The following combinations give rise to black seed coats:
A-B-C-
A-bbC-
A-B-cc
A-bbcc The following combinations give rise to brown seed coats:
aaB-cc
aaB-C-
aabbC- The gene combination needed for yellow canola seeds is aabbcc.

To generate commercial seed of cultivars containing black seed coat soybeans, also referred to herein as "bsc", bsc soybean seeds could be mixed into commercial seed in at least the following ways. In one embodiment of the present invention, a mix could be generated in the field. Bsc soybean plants which are homozygous for the 'i' allele at the I locus would be planted in separate rows in the same field as cultivars containing proprietary traits that are being increased for commercial seed sale. A treatment would be applied to the yellow seed coat rows that promotes outcrossing. In a preferred embodiment, this treatment includes the application of a higher concentration of the herbicide than normally applied. This may cause a decline in male fertility which could result in higher outcrossing rates. One skilled in the art can appreciate that the number of generations necessarily depends on the outcrossing rate and the required percentage of bsc in the seed mix.

A second illustrative embodiment of the mixing method of the present invention includes a mechanical mix. A bsc soybean plant would be crossed with a yellow seed coat plant. The bsc progeny after several generations of self-pollination would be retained. A known amount of this seed would be added to the yellow seed coat variety. The number of generations required for self-pollination would depend on the total amount of trait-containing seed that would be commercialized and the required percentage of bsc in the seed mix.

A preferred illustrative embodiment of the mixing method of the present invention is a combination of the field mix and the mechanical mix techniques. Bsc seed would be mixed in commercial seed as described for the mechanical mix above, and bsc seed would be grown together with the commercial cultivar in the last season of seed increase prior to commercial sale. The field mix results in the generation and maintenance of a higher level of individual plants that are heterozygous for the bsc gene. This is desirable because it would help to preserve the presence of the marker phenotype despite selection against it. The mechanical mix approach will have a lower cost of goods of production. One skilled in the art will appreciate that the combined approach optimizes the advantages of both systems.

In an additional embodiment of the present invention, a certain proportion of the bsc seed is actually yellow when sold to growers. In the first year's harvest, it will yield black seed and will thus deter the practice of on-farm seed sorting between seed purchase and planting. An alternate approach to this embodiment is to incorporate a second dominant seed coat color gene in the black seed coat line. In a preferred embodiment, this seed coat color should only be expressed in the absence of the black phenotype which is the homozygous black gene state. A brown seed coat color could be used as the second seed coat color. F2 seeds derived from F1 hybrid could be rapidly and cost-effectively color sorted using a near-infrared spectrophotometer based on the presence of the brown seed coat color. Seed would be increased from these hybrids for a further generation (F3 generation). This could be done without the need for additional sorting or with ongoing sorting out of the homozygous yellow lines. The F3 generation would be used as the bsc source which ensures a reliable level of bsc seed and a sufficient proportion of heterozygotes to deter on-farm seed sorting. In an additional embodiment of the present invention the same approach as described above regarding the use of a second seed coat color gene may be applied wherein selection of F2 seed derived from heterozgyous F1 individuals would not be enabled by the presence of a second seed coat color gene, but by the detection of the color expressed in heterozygous individuals carrying the Ii genotype in the maternal plant with the use of an NIR machine described elsewhere.

In an additional embodiment of the present invention the same approach as described above regarding the detection of heterozygous individuals for use in a mechanical mix could be enabled through the incorporation of a gene that results in an altered plant phenotype, such as an altered leaf shape, enabling the selection of heterozygous F1 plants in the subsequent generation. This approach would involve incorporating the selectable dominant phenotype in the black seed coat donor line.

In an additional embodiment of the present invention the same approach as described above regarding the detection of heterozygous individuals for use in a mechanical mix could be enabled by mixing a herbicide resistant black seeded line with a yellow seeded line that is not herbicide resistant. The F1 plants could be selected in the next generation by employing two steps. First, the yellow seeds would be sorted from the black seeds using a color sorter (this would include homozygous yellow, and heterozygous yellow). Second, the yellow seeded plants would be sprayed with a herbicide the following generation. Only the F1 heterozygous plants would survive. Seed from these plants would be harvested and increased for a further two generations. In addition, it is possible that outcrossing could be increased by applying a low level of herbicide while the yellow seeded, non-herbicide resistant plants are flowering.

In another embodiment, herbicide resistant and black seed coat seeds would be mixed with non-herbicide resistant yellow seed coat seeds randomly and planted on a large scale in the field. A preferred range of the ratio of herbicide resistant seeds to black seeds is 10/90 to 90/10, but any mix level can be used. Additional preferred ratios are 30/70, 50/50, or 70/30. A preferred embodiment of this invention regards large scale seed production, meaning at least a hectare of seed, but the area of field used may be any size, depending on the amount of F1 seed production desired. A high planting rate would be beneficial, as it would result in a more efficient use of space, and a higher level of outcrossing among plants. Soybean plants outcross with each other within a row at a rate of approximately 1%. If the outcrossing levels are lower, then increasing the size of the first crossing block will compensate.

The field would be bulk harvested, and replanted. A higher seeding rate than the initial rate may be used, with a preferred rate being double the initial seeding rate. The 1% outcrossed plants, derived from pollen from the yellow conventional soybean plants fertilizing the black seeded herbicide resistant plants, and the pollen from the black seeded herbicide resistant plants fertilizing yellow conventional plants would give rise to F1 seeds that are black and yellow respectively. These would be replanted along with all the selfed seed. This field would be sprayed with the herbicide for which herbicide resistance existed in the parental material. This spray would eliminate all the selfed yellow conventional seed. The remaining seed would be harvested.

Because the seed coat color is recessive and maternally inherited, the F2 seed derived from the F1 plants, would all be yellow in color and the F1 plants that produced this F2 seed would all be herbicide resistant. The F2 seed would be separated from the selfed black, herbicide resistant seed through the use of a color sorter, such as a Technicon near-infrared reflectance (NIR) spectrophotometer calibrated to determine total light reflectance (optical density) from 550 to 650 nanometers. The yellow seed would be retained.

The yellow F2 seed could be increased a further generation, or up to five generations, in the presence of further herbicide resistance selection in order to increase the amount of seed produced, and then could be mixed with seeds containing proprietary traits as a segregating phenotypic marker. Yellow F2 seed could also be directly used as a seed mixture, without further increases. This strategy would be equally effective if performed with a mix of non-herbicide resistant black seed lines with herbicide resistant yellow seeded lines.

Licensing fees may be calculated and collected from different entities who use or collect the seed. In one embodiment of the fee calculation procedure of the present invention, the growers would agree to pay part or all of the licensing fee owed for use of the proprietary technology upon delivery of grain containing the proprietary trait. Growers would agree to deliver grain with the proprietary trait only to designated elevators that have agreed to collect a fee for the proprietary trait. Growers would agree not to sort grain in a manner that would prevent or hinder detection of the marker phenotype or phenotypes. The license terms could apply to all grain produced from certified seed and grain from all subsequent generations. The grower may be issued a voucher upon payment of the fee which can be redeemed at the proprietor of the trait to receive discounts or other incentives on subsequent seed or chemical purchases.

In another embodiment of the method of fee collection of the present invention, the elevators would agree to collect a fee for grain containing the proprietary trait and to remit a portion of this fee to the proprietor of the trait. Elevators would also agree to allow access to their facilities by representatives from the proprietor of the trait to oversee the collection of trait fees and/or to audit grain inventories for the presence of grain with the proprietary trait. In an additional embodiment, the elevators could have all of the client account information stored on computers, and customized software would facilitate record keeping and fee assessment. This information could then be forwarded to the proprietor's computers via a network connection or the internet for record keeping, billing of either the grower or the elevator, and accounting purposes.

Seed sampling and testing protocols should be well known to one of skill in the art as indicated in the commonly used reference *International Rules for Seed Testing* 1999, available from the International Seed Testing Organization, all of the contents of which are hereby incorporated herein by reference. In an embodiment of the present invention, visual seed sampling may be used as a qualitative measurement standard. The grower would have a 0.25% threshold as a bottom level for detection. If the grower exceeds this threshold for a particular grain delivery to the elevator, then he or she pays licensing fees based on the amount of grain delivered. If the threshold is exceeded, but the grower protests the positive result for bsc, then a more specific test will be performed to determine if the grain contains the proprietary trait.

In an additional embodiment, the threshold values may be applied in a quantitative determination of the amount of bsc present. Threshold ranges such as 0.25% to 0.5% vs. 0.5% to 0.75% may be used to determine the proprietary trait fee based on the amount of bsc delivered to the elevator.

In view of the above, one of skill in the art should appreciate the usefulness of the above described method. Further, one of skill in the art should recognize that the method of the present invention may be applied to crops other than soybeans such as canola. A mixture of yellow canola seeds with a black seeded canola line carrying a proprietary trait would enable trait fee collection and tracking of proprietary traits at the point of delivery in a manner identical to what is proposed for soybean. The blue aleurone of wheat and/or the purple seed coat color may also be used a similar manner. Utilizing the methods of the present invention, phenotypic markers may also be used with proprietary corn and cotton. The use of phenotypic markers should be within the skill of one in the plant genetic arts and the usefulness of the present invention should be apparent to such a person.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

General Information Relevant to the Examples

The following term is used in describing the following examples:

"Roundup Ultra®" is the trade name for a common glyphosate herbicide

"OC" is outcrossing

EXAMPLE 1

The following example outlines a protocol for determining whether it is possible to enhance outcrossing in soybeans. Roundup® is used in treatments 2-7 at the amounts specified.

TABLE 1

| Quantity of Roundup ® | | Spray Schedule |
|---|---|---|
| Treatment 1 | unsprayed check | Roundup ® may be used for weed control |
| Treatment 2 | 80 oz/acre | 1-2 weeks before flowering |
| Treatment 3 | 64 oz/acre | Twice, once 3-4 weeks before flowering and once 1-2 weeks before flowering |

TABLE 1-continued

| Quantity of Roundup ® | | Spray Schedule |
|---|---|---|
| Treatment 4 | 96 oz/acre | 1-2 weeks before flowering |
| Treatment 5 | 80 oz/acre | Twice, once 3-4 weeks before flowering and once 1-2 weeks before flowering. |
| Treatment 6 | 80 oz/acre | 1-2 weeks before flowering |
| Treatment 7 | 80 oz/acre | Twice, once 3-4 weeks before flowering and once 1-2 weeks before flowering. |
| Treatment 8 | unsprayed check | Roundup ® may be used for weed control |

Treatments 1 to 5 contain black and yellow seeded plants in separate rows
Treatments 6 to 8 contain black and yellow seeded plants in the same rows Upon review of the above, one skilled in the art should recognize that the above method of applying high doses of herbicide should decrease male fertility and thus increase outcrossing.

EXAMPLE 2

The following example provides evidence for the reduction of male fertility in cotton plants resistant to Roundup®. Roundup Ultra® was sprayed over the top of the plants four times at the following intervals: 31, 45, 58, and 73 days post sowing. There were three different plots of plants and each plot received a different rate of Roundup Ultra® as follows: 0, 16, and 24 ounces/acre. Evaluation for male sterility was made 2 to 3 times per week for 7 weeks. Ten blooms per plot were hand-pollinated on each of 10 days. A fertility score of 1 to 5 was given to each plant where a score of 3-5 is considered fertile and less than 3 is considered sterile. Table 2 shows the results of this study.

TABLE 2

| Days Post-Sowing | Fertility Score of 0 oz/acre Roundup ® | Fertility Score of 16 oz/acre Roundup ® | Fertility Score of 24 oz/acre Roundup |
|---|---|---|---|
| 66 | 4.7 | 1.5 | 1.5 |
| 69 | 4.7 | 1.8 | 1.9 |
| 71 | 4.7 | 1.6 | 1.7 |
| 73 | 4.7 | 1.9 | 2.3 |
| 75 | 4.5 | 2.8 | 1.6 |
| 80 | 4.3 | 2.2 | 2.0 |
| 82 | 4.6 | 1.4 | 1.3 |
| 85 | 4.3 | 2.8 | 1.7 |
| 89 | 4.6 | 3.6 | 2.2 |
| 93 | 4.6 | 3.0 | 2.4 |
| 95 | 4.5 | 1.9 | 1.9 |
| 98 | 4.4 | 2.1 | 1.6 |
| 102 | 4.5 | 2.2 | 1.6 |
| 106 | 4.6 | 3.4 | 2.8 |
| 110 | 4.5 | 3.7 | 3.6 |

Upon review of the above, one skilled in the art should appreciate how male fertility is reduced in a dicotelydenous plant with high doses of herbicide and thus leading to higher outcrossing rates.

EXAMPLE 3

The following Table 3 shows the results of a model for a field mix of seed showing the percent of bsc soybean seeds in various generations of both the proprietor's commercial seed harvest and the growers harvest using a particular generation of the commercial seed. One row of bsc seed is planted between two rows of yellow seeds which means that the ratio of yellow seed to bsc seed is approximately 2:1 and an outcrossing rate of 5% is used. Only the yellow rows of seeds are harvested to generate the commercial cultivars.

TABLE 3

| Column/Row | (See Table 4) | B | C | D | E | F |
|---|---|---|---|---|---|---|
| | | Commercial Seed harvested | | | | |
| 6 | Generation # | II | Ii | ii | ii (black) | ii (yellow) |
| 7 | 1 | 95.00% | 5.00% | | | |
| 8 | 2 | 91.44% | 7.25% | 1.31% | | 1.31% |
| 9 | 3 | 88.59% | 8.20% | 3.22% | 1.31% | 1.90% |
| 10 | 4 | 86.10% | 8.53% | 5.37% | 3.22% | 2.15% |
| 11 | 5 | 83.82% | 8.57% | 7.61% | 5.37% | 2.24% |
| 12 | 6 | 81.67% | 8.48% | 9.86% | 7.61% | 2.25% |

| Column/Row | (See Table 5) | H | I | J | K | L |
|---|---|---|---|---|---|---|
| | | % BSC in grower's field | | | | |
| | | Year 1 | Year 2 | Year 3 | Year 4 | Year 5 |
| | Generation # | | | | | |
| 7 | 1 | 0.00% | 1.25% | 1.88% | 2.19% | 2.34% |
| 8 | 2 | 1.31% | 3.13% | 3.75% | 4.06% | 4.22% |
| 9 | 3 | 3.22% | 5.26% | 5.89% | 6.20% | 6.36% |
| 10 | 4 | 5.37% | 7.50% | 8.12% | 8.44% | 8.59% |
| 11 | 5 | 7.61% | 9.75% | 10.37% | 10.69% | 10.84% |
| 12 | 6 | 9.86% | 11.97% | 12.60% | 12.91% | 13.07% |

The formulas for the above model are as follows in Tables 4 and 5 under corresponding rows and columns:

TABLE 4

| | A | B | C | D | E |
|---|---|---|---|---|---|
| 1 | BSC % in field | 0.33 | | | |
| 2 | Outcrossing rate | 0.05 | | | |
| 3 | | | | | |
| 4 | | | | | |
| 5 | | Seed harvested | | | |
| 6 | Generation # | II | Ii | ii | ii (black) |
| 7 | 1 | =1−(1*B2) | =1*B2 | | |
| 8 | 2 | =+B7−(B7*B$2)+0.25*(C7−(B$2*C7)) | =+(C7*0.5)−(B$2*C7*0.5)+B$2*B7+0.5*B$2*C7 | =0.25*(C7−C7*B$2)+(0.5*B$2*C7) | |
| 9 | 3 | =+B8−(B8*B$2)+0.25*(C8−(B$2*C8)) | =+(C8*0.5)−(B$2*C8*0.5)+B$2*B8+0.5*B$2*C8 | =0.25*(C8−C8*B$2)+(0.5*B$2*C8)+D8 | =+D8 |
| 10 | 4 | =+B9−(B9*B$2)+0.25*(C9−(B$2*C9)) | =+(C9*0.5)−(B$2*C9*0.5)+B$2*B9+0.5*B$2*C9 | =0.25*(C9−C9*B$2)+(0.5*B$2*C9)+D9 | =+D9 |
| 11 | 5 | =+B10−(B10*B$2)+0.25*(C10−(B$2*C10)) | =+(C10*0.5)−(B$2*C10*0.5)+B$2*B10+0.5*B$2*C10 | =0.25*(C10−C10*B$2)+(0.5*B$2*C10)+D10 | =+D10 |
| 12 | 6 | =+B11−(B11*B$2)+0.25*(C11−(B$2*C11)) | =+(C11*0.5)−(B$2*C11*0.5)+B$2*B11+0.5*B$2*C11 | =0.25*(C11−C11*B$2)+(0.5*B$2*C11)+D11 | =+D11 |

TABLE 5

| | F | G | H | I | J | K | L |
|---|---|---|---|---|---|---|---|
| 1 | | | | | | | |
| 2 | | | | | | | |
| 3 | | | | | | | |
| 4 | | | % B in grower's field | | | | |
| 5 | | | Year 1 | Year 2 | Year 3 | Year 4 | Year 5 |
| 6 | ii (yellow) | | | | | | |
| 7 | | =SUM(B7:D7) | =+D7 | =+H7+0.25*C7 | =+I7+0.25*0.5*C$7 | =+J7+0.25*0.25*C$7 | =+K7+0.25*0.125*C$7 |
| 8 | =+D8−D7 | =SUM(B8:D8) | =+D8 | =+H8+0.25*C8 | =+I8+0.25*0.5*C$7 | =+J8+0.25*0.25*C$7 | =+K8+0.25*0.125*C$7 |
| 9 | =+D9−D8 | =SUM(B9:D9) | =+D9 | =+H9+0.25*C9 | =+I9+0.25*0.5*C$7 | =+J9+0.25*0.25*C$7 | =+K9+0.25*0.125*C$7 |
| 10 | =+D10−D9 | =SUM(B10:D10) | =+D10 | =+H10+0.25*C10 | =+I10+0.25*0.5*C$7 | =+J10+0.25*0.25*C$7 | =+K10+0.25*0.125*C$7 |
| 11 | =+D11−D10 | =SUM(B11:D11) | =+D11 | =+H11+0.25*C11 | =+I11+0.25*0.5*C$7 | =+J11+0.25*0.25*C$7 | =+K11+0.25*0.125*C$7 |
| 12 | =+D12−D11 | =SUM(B12:D12) | =+D12 | =+H12+0.25*C12 | =+I12+0.25*0.5*C$7 | =+J12+0.25*0.25*C$7 | =+K12+0.25*0.125*C$7 |

In view of the above, one of skill in the art should recognize that the amount of black seed in the grower's field can be approximated through several generations. One can also note how many generations are necessary to generate a commercial seed cultivar that actually contains black seeds generated through outcrossing.

EXAMPLE 4

The following Tables 6 and 7 show the results of a model for a mechanical mix of seed showing the percent of bsc soybean seeds in various generations of the proprietor's commercial seed harvest. This example of the model is based on producing enough seed such that a grower will harvest 3% bsc. The model predicts the amount of black seeds needed to mix with a particular generation of the commercial cultivar to obtain a mixture of seeds which will give the desired grower harvest of bsc. The model also shows how the number of black seed units produced varies depending on whether black seeds are sorted out of the mix.

Tables 8 and 9 show the model for the generation of Tables 6 and 7.

TABLE 6

| | A | B | C | D | E | F | G | H |
|---|---|---|---|---|---|---|---|---|
| 2 | | | | | | | BSC % | 3% |
| 3 | | | | | | | | |
| 4 | | Seed harvested | | total | black | yellow | | |
| 5 | Generation # | II | Ii | ii | ii | ii | | No sorting |
| 6 | F1 | 100% | | | | | | |
| 7 | F2 | 25% | 50% | 25% | 0% | 25% | | Mix rate |
| 8 | F3 | 37.50% | 25% | 37.50% | 25% | 12.50% | | 6.86% |
| 9 | F4 | 43.75% | 12.50% | 43.75% | 38% | 6.25% | | 6.40% |
| 10 | F5 | 46.88% | 6.25% | 46.88% | 44% | 3.13% | | 6.19% |
| 11 | | | | | | | | |

TABLE 6-continued

|    | A | B | C | D | E | F | G | H |
|----|---|---|---|---|---|---|---|---|
| 13 |   | Seed increase |   |   |   |   |   |   |
| 14 |   | # of seeds | Weight (kg) |   | 16 g/100 seeds |   | 0.00016 |   |
| 15 | F1 | 20 | 0.0032 |   |   |   |   |   |
| 16 | F2 | 1200 | 0.192 |   |   |   |   |   |
| 17 | F3 | 72000 | 11.52 |   |   |   |   |   |
| 18 | F4 | 4320000 | 691.2 |   |   |   |   |   |
| 19 | F5 | 259200000 | 41472 |   |   |   |   |   |
| 20 |   |   |   |   |   |   |   |   |
| 21 |   |   |   |   |   |   |   |   |
| 22 |   |   |   |   |   |   |   |   |
| 23 | Mechanical mix with a field mix |   |   |   |   |   |   |   |
| 24 | OC rate |   | 5% |   | total | black | yellow |   |
| 25 | Generation # | II | Ii | ii | ii | ii |   | No snorting |
| 26 | F1 |   | 100% |   |   |   |   |   |
| 27 | F2 | 23.75% | 50.00% | 26.25% | 0% | 26% |   |   |
| 28 | F3 | 34.44% | 26.19% | 39.38% | 26% | 13.13% |   | 6.53% |
| 29 | F4 | 38.94% | 14.82% | 46.25% | 39% | 6.87% |   | 6.01% |
| 30 | F5 | 40.51% | 9.35% | 50.14% | 46% | 3.89% |   | 5.72% |
| 31 |   |   |   |   |   |   |   |   |
| 32 |   |   |   |   |   |   |   |   |
| 33 |   | Seed increase |   |   |   |   |   |   |
| 34 |   | # of seeds | Weight (kg) |   | 16 g/100 seeds |   | 0.00016 |   |
| 35 | F1 | 20 | 0.0032 |   |   |   |   |   |
| 36 | F2 | 1200 | 0.192 |   |   |   |   |   |
| 37 | F3 | 72000 | 11.52 |   |   |   |   |   |
| 38 | F4 | 4320000 | 691.2 |   |   |   |   |   |
| 39 | F5 | 259200000 | 41472 |   |   |   |   |   |

TABLE 7

|    | I | J | K | L | M | N | O |
|----|---|---|---|---|---|---|---|
| 2  |   |   |   |   |   |   |   |
| 3  |   |   |   |   |   |   |   |
| 4  |   |   |   |   |   |   |   |
| 5  | Units produced with mix | Remove black | Units produced with mix | Select hetero's and blacks | Units produced with mix | Select hetero's | Units produced with mix |
| 6  |   |   |   |   |   |   |   |
| 7  |   | Mix rate |   | Mix rate |   | Mix rate |   |
| 8  | 6.72 | 12.00% | 3.84 | 4.29% | 10.75 | 48.00% | 0.96 |
| 9  | 432 | 20.00% | 138.24 | 3.60% | 768.00 | 96.00% | 28.8 |
| 10 | 26784 | 36.00% | 4608 | 3.29% | 50416.94 | 192.00% | 864 |
| 11 |   |   |   |   |   |   |   |
| 12 |   |   |   |   |   |   |   |
| 13 |   |   |   |   |   |   |   |
| 14 |   |   |   |   |   |   |   |
| 15 |   |   |   |   |   |   |   |
| 16 |   |   |   |   |   |   |   |
| 17 |   |   |   |   |   |   |   |
| 18 |   |   |   |   |   |   |   |
| 19 |   |   |   |   |   |   |   |
| 20 |   |   |   |   |   |   |   |
| 21 |   |   |   |   |   |   |   |
| 22 |   |   |   |   |   |   |   |
| 23 |   |   |   |   |   |   |   |
| 24 |   |   |   |   |   |   |   |
| 25 | Units produced with mix | Remove black | Units produced with mix | Select hetero's and blacks | Units produced with mix | Select hetero's | Units produced with mix |
| 26 |   |   |   |   |   |   |   |
| 27 |   |   |   |   |   |   |   |
| 28 | 7.05 | 11.25% | 4.10 | 4.28% | 10.76 | 48.09% | 0.96 |
| 29 | 460.37 | 17.19% | 160.80 | 3.67% | 753.90 | 86.92% | 31.81 |
| 30 | 29017.66 | 25.89% | 6406.78 | 3.40% | 48775.01 | 140.63% | 1179.57 |

TABLE 8

| | A | B | C | D | E | F |
|---|---|---|---|---|---|---|
| | | Seed harvested | | total | black | yellow |
| 4 | | | | | | |
| 5 | Generation # | II | Ii | ii | ii | ii |
| 6 | F1 | | 1 | | | |
| 7 | F2 | 0.25 | 0.5 | 0.25 | =+D7−F7 | =+D7 |
| 8 | F3 | 0.375 | 0.25 | 0.375 | =+D8−F8 | =+D8−D7 |
| 9 | F4 | =+B8+0.25*C8 | =+C8*0.5 | =+D8+0.25*C8 | =+D9−F9 | =+D9−D8 |
| 10 | F5 | =+B9+0.25*C9 | =+C9*0.5 | =+D9+0.25*C9 | =+D10−F10 | =+D10−D9 |
| 11 | | | | | | |
| 12 | | | | | | |
| 13 | | Seed increase | | | | |
| 14 | | # of seeds | Weight (kg) | | 16 g/100 seeds | |
| 15 | F1 | 20 | =+B15*G14 | | | |
| 16 | F2 | =+B15*60 | =+B16*G14 | | | |
| 17 | F3 | =+B16*60 | =+B17*G14 | | | |
| 18 | F4 | =+B17*60 | =+B18*G14 | | | |
| 19 | F5 | =+B18*60 | =+B19*G14 | | | |
| 20 | | | | | | |
| 21 | | | | | | |
| 22 | | | | | | |
| 23 | Mechanical mix with a field mix | | | | | |
| 24 | OC rate | 0.05 | | total | black | yellow |
| 25 | Generation # | II | Ii | ii | ii | ii |
| 26 | F1 | | 1 | | | |
| 27 | F2 | =0.25*(C26−C26*B$24)+B26−B$24*B26 | =0.5*(C26−C26*B$24)+B$24*B26+0.5*C26*B$24 | =0.25*(C6−C26*B$24)+0.5*B$24*C26+D26 | =+D27−F27 | =+D27 |
| 28 | F3 | =0.25*(C27−C27*B$24)+B27−B$24*B27 | =0.5*(C27−C27*B$24)+B$24*B27+0.5*C27*B$24 | =0.25*(C27−C27*B$24)+0.5*B$24*C27+D27 | =+D28−F28 | =+D28−D27 |
| 29 | F4 | =0.25*(C28−C28*B$24)+B28−B$24*B28 | =0.5*(C28−C28*B$24)+B$24*B28+0.5*C28*B$24 | =0.25*(C28−C28*B$24)+0.5*B$24*C28+D28 | =+D29−F29 | =+D29−D28 |
| 30 | F5 | =0.25*(C29−C29*B$24)+B29−B$24*B29 | =0.5*(C29−C29*B$24)+B$24*B29+0.5*C29*B$24 | =0.25*(C29−C29*B$24)+0.5*B$24*C29+D29 | =+D30−F30 | =+D30−D29 |
| 31 | | | | | | |
| 32 | | | | | | |
| 33 | | Seed increase | | | | |
| 34 | | # of seeds | Weight (kg) | | 16 g/100 seeds | |
| 35 | F1 | 20 | 0.0032 | | | |
| 36 | F2 | 1200 | 0.192 | | | |
| 37 | F3 | 72000 | 11.52 | | | |
| 38 | F4 | 432000 | 691.2 | | | |
| 39 | F5 | 259200000 | 41472 | | | |

TABLE 9

| | G | H | I | J | K | L | M | N | O |
|---|---|---|---|---|---|---|---|---|---|
| 1 | | | | | | | | | |
| 2 | BSC % | 0.03 | | | | | | | |
| 3 | | | | | | | | | |
| 4 | | | | | | | | | |
| 5 | | | No sorting | Units produced with mix | Remove black | Units produced with mix | Select hetero's and blacks | Units produced with mix | Select hetero's | Units produced with mix |
| 6 | | | | | | | | | |
| 7 | | | Mix rate | | Mix rate | | Mix rate | | Mixed rate | |
| 8 | | =+H$2/(0.25*C8+D8) | =+C17/(H8*25) | =+H$2/((F8+0.25*C8)/(1−E8)) | =+C17/(J8*25) | =+H$2/((0.25*C8+D8)/(1−B8)) | =+C17/(L8*25) | =+H$2/((0.25*C8)/(1−B8+D8)) | =+C17/(N8*25) |
| 9 | | =+H$2/(0.25*C9+D9) | =+C18/(H9*25) | =+H$2/((F9+0.25*C9)/(1−E9)) | =+C18/(J9*25) | =+H$2/((0.25*C9+D9)/(1−B9)) | =+C18/(L9*25) | =+H$2/((0.25*C9)/(1−B9+D9)) | =+C18/(N9*25) |
| 10 | | =+H$2/(0.25*C10+D10) | =+C19/(H10*25) | =+H$2/((F10+0.25*C10)/(1(1−E10)) | =+C19/(J10*25) | =+H$2/((0.25*C10+D10)/(1−B10)) | =+C19/(L10*25) | =+H$2/((0.25*C10)/(1−B10+D10)) | =+C19/(N10*25) |
| 11 | | | | | | | | | |
| 12 | | | | | | | | | |
| 13 | | | | | | | | | |

TABLE 9-continued

| | G | H | I | J | K | L | M | N | O |
|---|---|---|---|---|---|---|---|---|---|
| 14 | =0.016/100 | | | | | | | | |
| 15 | | | | | | | | | |
| 16 | | | | | | | | | |
| 17 | | | | | | | | | |
| 18 | | | | | | | | | |
| 19 | | | | | | | | | |
| 20 | | | | | | | | | |
| 21 | | | | | | | | | |
| 22 | | | | | | | | | |
| 23 | | | | | | | | | |
| 24 | | | | | | | | | |
| 25 | | No sorting | Units produced | Remove black | Units produced | Select hetero's | Units produced | Select hetero's | Units produced |
| 26 | | | with mix | | with mix | and blacks | with mix | | with mix |
| 27 | | | | | | | | | |
| 28 | | =+H$2/(0.25*C28+D28) | =+C37/(H28*25) | =+H$2/F28+0.25*C28)/(1−E28)) | =+C37/(J28*25) | =+H$2/((0.25*C28+D28)/(1−B28)) | =+C37/(L28*25) | =+H$2/((0.25*C28)/(1−B28+D28)) | =+C37/(N28*25) |
| 29 | | =+H$2/(0.25*C29+D29) | =+C38/(H29*25) | =+H$2/F29+0.25*C29)/(1−E29)) | =+C38/(J29*25) | =+H$2/((0.25*C29+D29)/(1−B29)) | =+C38/(L29*25) | =+H$2/((0.25*C29)/(1−B29+D29)) | =+C38/(N29*25) |
| 30 | | =+H$2/(0.25*C30+D30) | =+C39/(H30*25) | =+H$2/F30+0.25*C30)/(1−E30)) | =+C39/(J30*25) | =+H$2/((0.25*C30+D30)/(1−B30)) | =+C39/(L30*25) | =+H$2/((0.25*C30)/(1−B30+D30)) | =+C39/(N30*25) |
| 31 | | | | | | | | | |
| 32 | | | | | | | | | |
| 33 | | | | | | | | | |
| 34 | 0.00016 | | | | | | | | |

EXAMPLE 5

In the following example licensing fees are calculated for a delivery of grain by the grower to the elevator. The bsc level is set to be 2% in trait fee hectares. The total grain amount is 1000 metric tons. The fraction of bsc in the delivery to the elevator is 0.8%. The current commodity price for standard soybean is $100/metric ton. The trait fee is assessed as a 2.5% premium over commodity price on the grain containing the proprietary trait. Thus, licensing fees may be assessed in the following manner:

First, the elevator determines whether the grain shipment contains the proprietary trait based on the presence of bsc in the grain. Then the elevator performs the following set of calculations to determine the trait fee:

The fraction of grain with the proprietary trait = 0.8%/2.0% = 0.4

The grain amount with the proprietary trait = 1000 metric tons × 0.4
= 400 metric tons The trait fee = (grain with trait) × (commodity price) ×
(trait fee premium %)
= (400 metric tons) × ($100/metric ton) × (2.5%)
= $1,000

In view of the above, one of skill in the art should recognize that the grower is only paying a proprietary trait fee based on the amount of proprietary grain present.

EXAMPLE 6

A method for using mechanical mixing to generate levels of heterozygous bsc seeds that will deter seed sorting by growers is as follows:

Step #1  Plant a known quantity of mixed seed which is homozygous yellow and homozygous black of the same maturity over a significant area, 10 acres or more, at a high density in which the plants are crowded within a row.
Step #2  Harvest all seed produced from this mixed planting. 0.5 to 1% of the yellow seed harvested should be heterozygous for the "I" gene(Ii) and thus still yellow, but with a little more black or gray color, especially in and/or around the hilum.
Step #3  The harvested seed will be replanted and F1 plants selected based on the presence of a dominant trait (leaf morphology, or a second herbicide resistance).
Step #4  The heterozygous yellow seed will be harvested and increased for a further generation.
Step #5  The seed increased and sorted as a result of the steps above would be mixed into varietal seed containing a proprietary trait.

In view of the above, one of skill in the art should recognize that seed sorting of the mixture in Step 5 will be very difficult for the grower to accomplish.

EXAMPLE 7

A method for using mechanical mixing to generate levels of heterozygous bsc seeds that will deter seed sorting is as follows:

Step #1  Plant a known quantity of mixed seed which is homozygous yellow and homozygous black of the same approximate-maturity over a significant area (e.g., 10 acres or more) at a high density in which the plants are crowded within a row.
Step #2  Harvest all seed produced from this mixed planting. 0.5 to 1% of the yellow seed harvested should be heterozygous for the "I" gene(Ii) but all seed from the yellow seeded lines will be yellow, and all seed from the black seeded lines will be black, due to the maternal control of seed coat color.
Step #3  All harvested seed would be replanted.
Step #4  Heterozygous yellow seed will be identified either through the use of a dominant plant phenotype (leaf shape, or second herbicide resistance), or through the harvest of seed that exhibits

| | |
|---|---|
| | a slight coloring due to the heterozygous nature of the parental plants. These F2 seeds would be replanted and increased for a further generation. |
| Step #5 | The seed increased and sorted as a result of the steps above would be mixed with bsc seed that is simply increased and varietal yellow seed containing a proprietary trait. |

Alternatives:

The homozygous yellow seeds would not need to be sorted out from the increases following the first initial sorting. The mixture level would be adjusted to compensate for the presence of this seed. This does not affect the amount of black or heterozygous seed sold to or harvested by the grower.

In view of the above, one of skill in the art should recognize that seed sorting of the mixture in Step 5 will be very difficult for the grower to accomplish.

EXAMPLE 8

A large scale method for generating hybrid soybean seed is as follows:

| Step #1 | Herbicide resistant, black seed coat seeds are mixed in a 50/50 seed mixture with non-herbicide resistant yellow seed coat seeds, and randomly planted on a field large enough to produce at least a hectare of F1 seed. There should be approximately 1% outcrossing. |
|---|---|
| Step #2 | The field is bulk harvested and the seeds are replanted in the field at double the seeding rate. The resulting outcrossed seeds are replanted with the selfed seed. |
| Step #3 | The field is sprayed with the herbicide for which herbicide resistance existed in the parental material. This will eliminate all of the selfed yellow conventional seed. |
| Step #4 | The remaining seed is harvested. The F2 seed is separated from the selfed black, herbicide resistant seed through the use of a color sorter. The yellow seed is retained. |
| Step #5 | The yellow seed from step 4 (F2 seed) is increased and then used to mix with seeds containing proprietary traits as a segregating phenotypic marker. |

In view of the above, one of skill in the art should recognize that seed sorting of the mixture in Step 5 will be very difficult for the grower to accomplish.

EXAMPLE 9

The following Tables 10 and 11 show a model for a large scale method for generating hybrid soybean seed described in Example 8. Table 10 contains the results and Table 11 shows the appropriate formulas:

TABLE 10

| A | B | C | D | E |
|---|---|---|---|---|
| 1 | | | | |
| 2 | Inputs | | | |
| 3 Field size (Ha) | 10 | | | |
| 4 Planting rate (seeds/Ha) | 300000 | | | |
| 5 Outcrossing rate (%) | 1% | | | |
| 6 Increase rate (X) | 40 | | | |
| 7 Mixing rate (%) | 2% | | | |
| 8 | | | | |
| 9 | Seeds | Kg | Units | Mixed units |
| 10 F1 seed produced | 1200000 | 180 | 7.2 | 360 |
| 11 F2 seed produced | 36000000 | 5400 | 216 | 10800 |
| 12 F3 seed produced | 1200000000 | 180000 | 7200 | 360000 |

TABLE 11

| A | B | C | D | E |
|---|---|---|---|---|
| 1 | | | | |
| 2 | Inputs | | | |
| 3 Field size (Ha) | 10 | | | |
| 4 Planting rate (seeds/Ha) | 300000 | | | |
| 5 Outcrossing rate (%) | 0.01 | | | |
| 6 Increase rate (X) | 40 | | | |
| 7 Mixing rate (%) | 0.02 | | | |
| 8 | | | | |
| 9 | Seeds | Kg | Units | Mixed units |
| 10 F1 seed produced | =+B3*B4*B5*B6 | =+B10*0.00015 | =+C10/25 | =+D10/B$7 |
| 11 F2 seed produced | =+B10*B6*0.75 | =+B11*0.00015 | =+C11/25 | =+D11/B$7 |
| 12 F3 seed produced | =+(2/3*B11*B6*0.75)+ (1/3*B11*B6) | =+B12*0.00015 | =+C12/25 | =+D12/B$7 |

Note: The weight of 1 seed is 0.00015 kg.
1 unit = 25 Kg

EXAMPLE 10

The following large scale method for generating hybrid soybean seed utilizes the model in Example 9 above:

| Step #1 | Hybrid Production nursery | |
|---|---|---|
| | Size: | 10 Ha |
| | Planting rate: | 300,000 seeds/Ha |
| | Roundup ® spray: | No |
| | Harvest all: | 300,000 × 5 × 40 = 360 units |
| Step #2 | Select hybrid progeny (grow F1 plants and harvest F2 seed) | |
| | Size: | 120 Ha |
| | Planting rate: | 300,000 seeds/Ha |
| | Roundup ® spray: | Early |
| | Harvest all remaining: | 7,272 units |
| Step #3 | Select F2 seed and recycle black RR seed | |
| | Seed selected as yellow/RR = 144 units | |

-continued

| Step #4 | Final production of product for mixing (grow F2 plants) | |
| --- | --- | --- |
| | Size: | 240 Ha |
| | Planting rate: | 100,000 seeds/Ha |
| | Roundup ® spray: | Early |
| | Harvest all: | 4,320 units |
| Step #5 | Mechanical mixing | |
| | Mix product of Step #4 with commercial seed at a 2% rate. | |

When farmers plant the mix generated by Step #5, the resulting harvest will contain approximately 0.63% black seed.

REFERENCES

The following references, to the extent that they provide exemplary procedural or other details supplementary to those set forth herein, are specifically incorporated herein by reference.

Nagai, I. 1921. A gentico-physiological study on the formation of anthocyanin and brown pigments in plants. *Tokyo Univ. Coll. of Agr. J* 8:1-92

Woodworth C. M., 1921. Inheritance of cotyledon, seed coat, hilum, and pubescence colors in soy-beans. *Genetics* 6:487-553.

Williams L. F. 1952. The inheritance of certain black and brown pigments in the soy-bean. *Genetics* 37: 208-215.

Nagai I. and S. Saite. 1923. Linked Factors in Soybeans. *Jap. J Bot.* 1:-121-136.

Williams L. F. 1958. Alteration of dominance and apparent change indirection of gene action by a mutation at another locus affecting the pigmentation of the seed coat of the soybean (Abs.) *Tenth Int. Cong. Genet. Proc.* 2:315-316.

Williams L. F. 1945. Off-colored seeds in the Lincoln soybean. *Soybean Digest* 5(11) 51-61.

*International Rules for Seed Testing* 1999 (Seed Science and Technology, Vol.27, Supplement, 1999) International Seed Testing Organization Van Deynze A. and Pauls, Peter. 1994. "The inheritance of seed color and vernalization requirement in *Brassica napus* using doubled haploid populations," *Euphytica* 74:77-83.

What is claimed is:

1. A method of preparing a soybean seed mix, wherein all the seed of the mix have a genetically modified trait and a fraction of the seed is heterozygous or homozygous for seed coat color, the method comprising:

i) planting homozygote black seed coat soybean plants having genotype RRiiTT in separate, alternate rows in the same field as cultivars that have a genetically modified trait and that are not homozygote black seed coat soybean plants;

ii) harvesting grain from the rows planted with the cultivars that contain the genetically modified trait and that are not homozygote black seed coat soybean plants; and iii) replanting the grain in separate, alternate rows in the same field as homozygote black seed coat soybean plants having genotype RRiiTT and harvesting the grain over at least one additional generation; wherein only the rows planted with the grain are harvested;

wherein the grain obtained from step iii constitutes a soybean seed mix.

2. The method of claim 1 further comprising:

iv) separating the black seed coat seeds from the harvested grain of step iii);

v) propagating the black seed coat seeds through at least one generation of self-pollination; and vi) mixing a known quantity of the propagated black seed coat seed with seed of a commercial cultivar having the genetically modified trait.

3. The method of claim 2, further comprising growing the mixture containing a known quantity of black seed coat seeds with the commercial cultivar seeds in the last season of seed increase prior to commercial sale.

4. The method of claim 1, wherein the genetically modified trait is herbicide resistance.

5. The method of claim 4, wherein the genetically modified trait is glyphosate resistance.

6. The method of claim 4, wherein cross-pollination of the cultivar having the genetically modified trait by the black seed coat soybean plants is promoted by treating the rows of said cultivar with a herbicide.

7. The method of claim 6, wherein the herbicide is glyphosate.

8. The method of claim 1, wherein with step i) the coat color of seeds from the cultivar having the genetically modified trait is yellow.

9. The method of claim 2, wherein the coat color of the commercial cultivar seeds is yellow.

10. The method of claim 2, wherein the seed mix obtained from step vi comprises between about 0.1% to about 10% by weight black seed coat seed.

11. The method of claim 10, wherein the seed mix obtained from step vi comprises between about 0.5% to about 4% by weight black seed coat seed.

\* \* \* \* \*